United States Patent
Hong

(10) Patent No.: US 12,092,603 B2
(45) Date of Patent: Sep. 17, 2024

(54) COMBUSTION ANALYZER

(71) Applicant: Fieldpiece Instruments, Inc., Orange, CA (US)

(72) Inventor: Tinggui Hong, Orange, CA (US)

(73) Assignee: Fieldpiece Instruments, Inc., Orange, CA (US)

( * ) Notice: Subject to any disclaimer, the term of this patent is extended or adjusted under 35 U.S.C. 154(b) by 0 days.

(21) Appl. No.: 18/244,268

(22) Filed: Sep. 10, 2023

(65) Prior Publication Data

US 2023/0417699 A1    Dec. 28, 2023

Related U.S. Application Data

(63) Continuation of application No. 17/166,888, filed on Feb. 3, 2021, now Pat. No. 11,788,986, which is a continuation-in-part of application No. 16/407,807, filed on May 9, 2019.

(60) Provisional application No. 62/676,804, filed on May 25, 2018.

(51) Int. Cl.
*G01N 27/416* (2006.01)
*G01N 1/22* (2006.01)

(52) U.S. Cl.
CPC ......... *G01N 27/416* (2013.01); *G01N 1/2205* (2013.01); *G01N 1/2258* (2013.01); *G01N 2001/2261* (2013.01); *G01N 2001/227* (2013.01); *G01N 2001/2282* (2013.01)

(58) Field of Classification Search
None
See application file for complete search history.

(56) References Cited

U.S. PATENT DOCUMENTS

| | | | | |
|---|---|---|---|---|
| 3,950,136 A * | 4/1976 | Bellinga | ............... | G01N 1/22 422/83 |
| 3,960,500 A * | 6/1976 | Ross | ............... | G01N 1/2258 73/23.31 |
| 3,985,624 A * | 10/1976 | Prevost | ............... | B01D 3/4261 203/1 |
| 4,073,619 A * | 2/1978 | Lawson | ............... | B01D 53/30 422/62 |
| 4,485,684 A * | 12/1984 | Weber | ............... | G01N 1/2247 73/863.11 |
| 4,561,288 A * | 12/1985 | Moenkhaus | ....... | G01N 33/0032 73/23.31 |
| 7,029,920 B2 * | 4/2006 | Lanier | ............... | G01N 33/0037 436/118 |
| 7,588,726 B1 * | 9/2009 | Mouradian | ........ | G01N 33/0009 702/22 |
| 9,846,107 B1 * | 12/2017 | D'Amico | ............... | G01M 99/00 |
| 10,837,877 B2 * | 11/2020 | Siperstein | ............ | G01N 1/2214 |

(Continued)

FOREIGN PATENT DOCUMENTS

| DE | 19855831 A | * | 3/2000 | |
| GB | 2169726 A | * | 7/1986 | ............. F23N 5/003 |

*Primary Examiner* — Daniel S Larkin
(74) *Attorney, Agent, or Firm* — Paul J. Backofen

(57) ABSTRACT

A combustion analyzer system includes an analyzer unit, a primary analysis probe and one or more remote probes. The analyzer unit includes a condensation removal unit and two or more electrochemical sensors to detect at least oxygen and carbon monoxide. The analyzer unit or the primary analysis probe include a means for condensing and eliminating liquid in the combustion gas to be analyzed.

18 Claims, 13 Drawing Sheets

(56) References Cited

U.S. PATENT DOCUMENTS

| | | | |
|---|---|---|---|
| 2014/0250975 A1* | 9/2014 | Kane | G01N 1/2205 73/23.31 |
| 2018/0280191 A1* | 10/2018 | Taylor | A61F 7/0053 |

\* cited by examiner

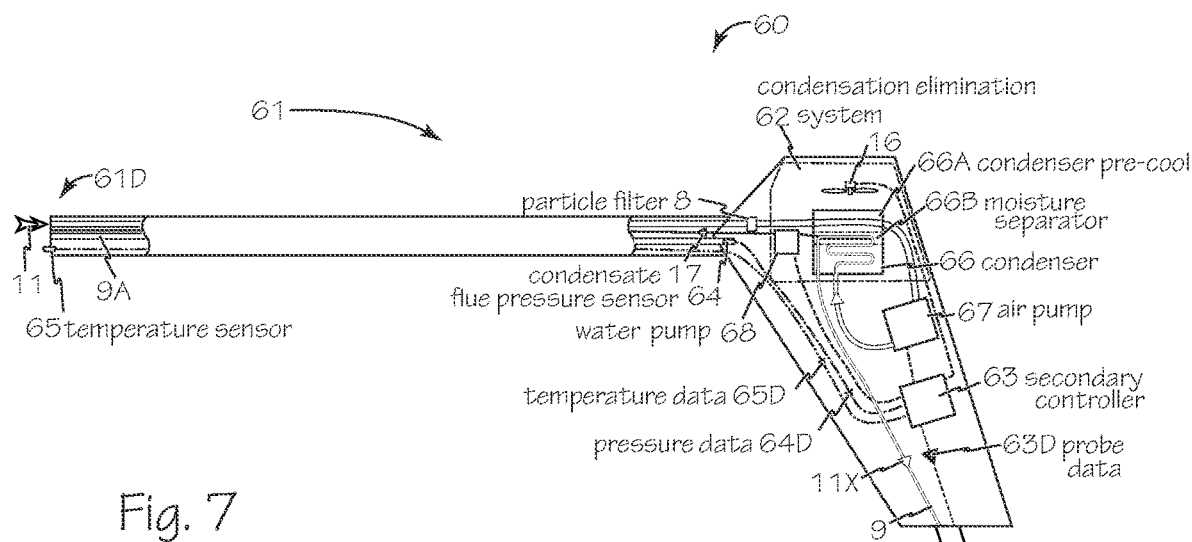
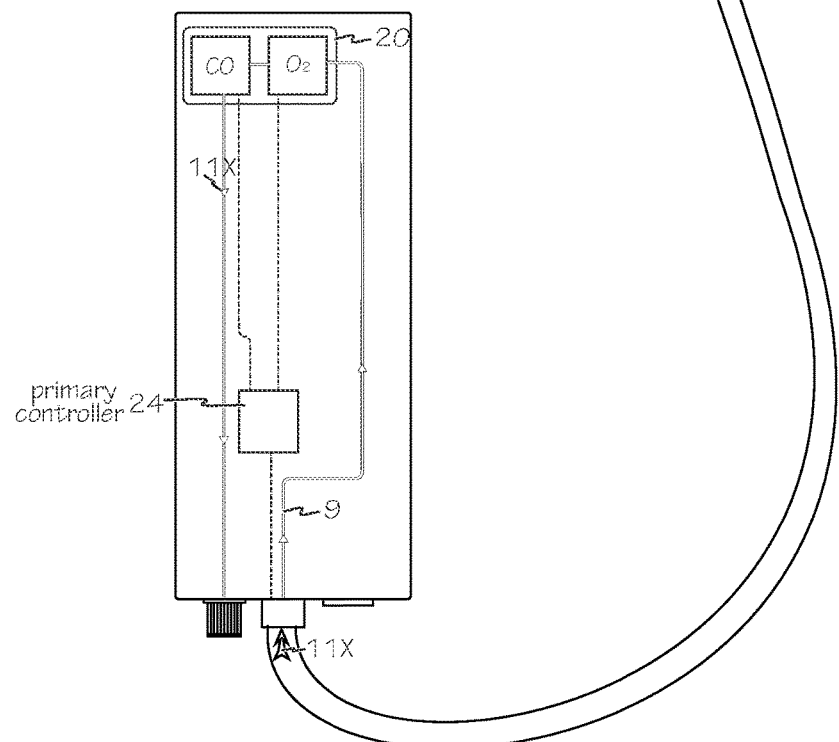
Fig. 7

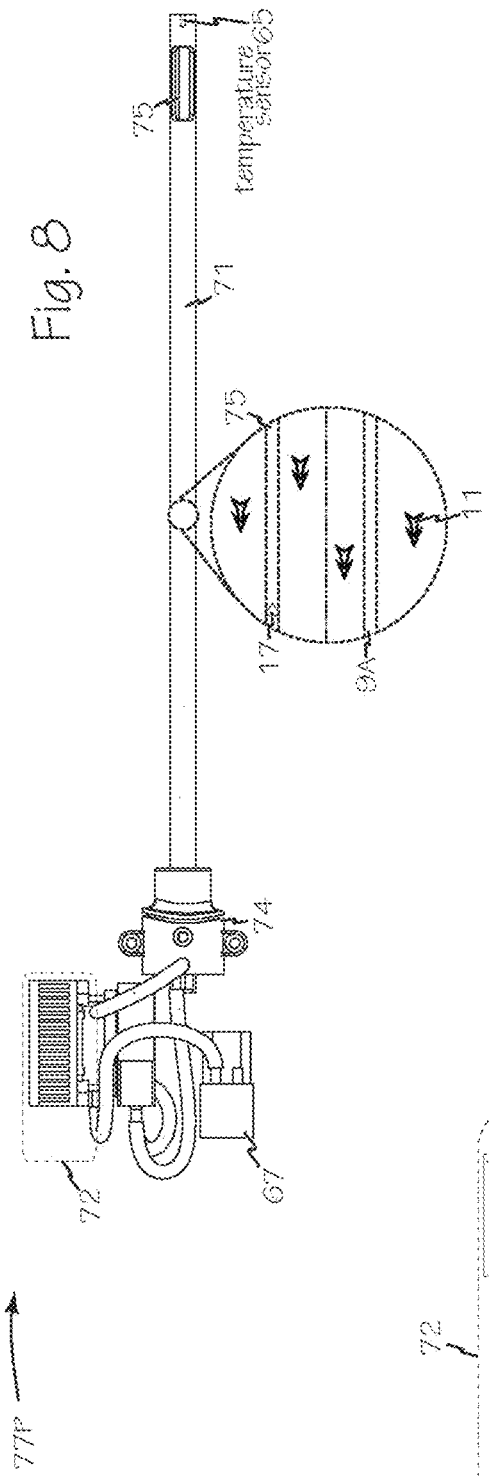
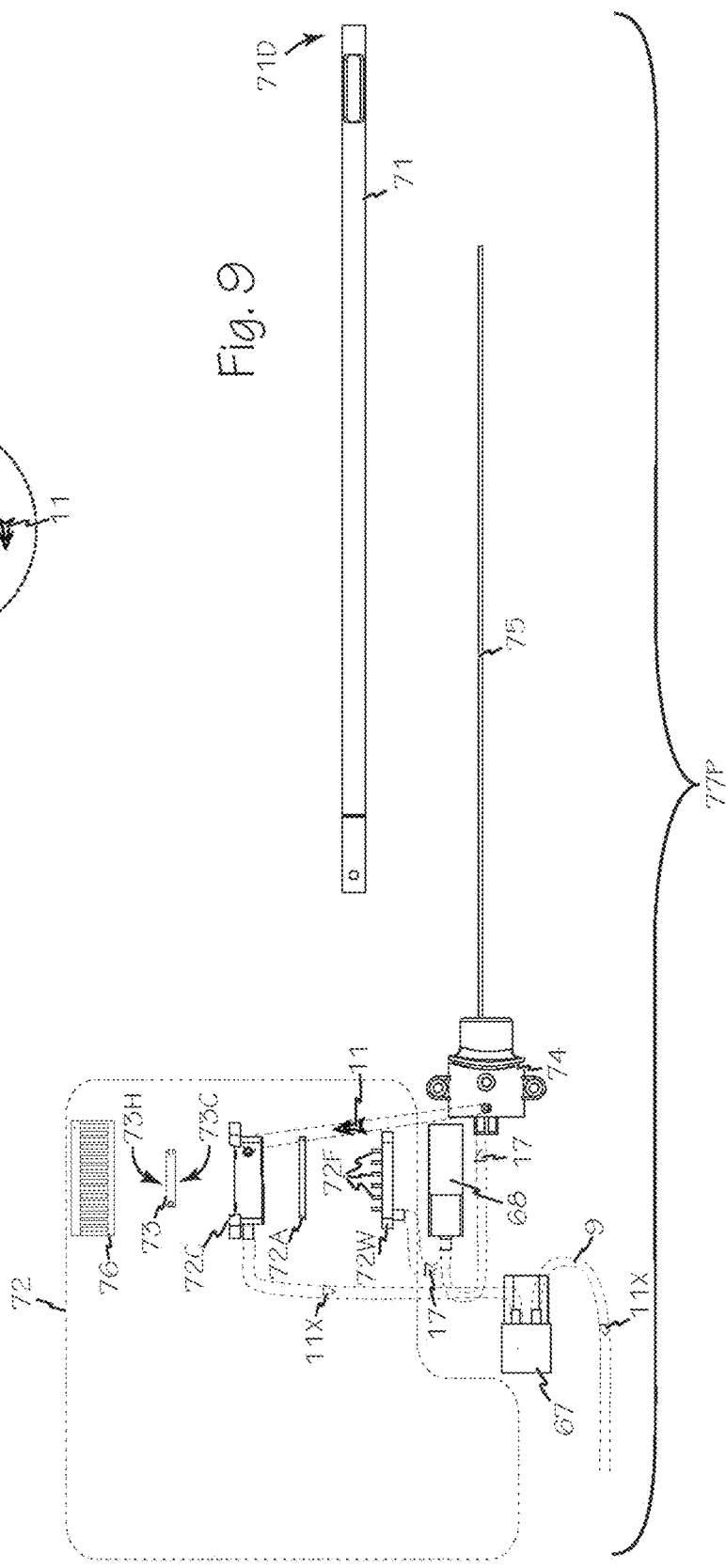

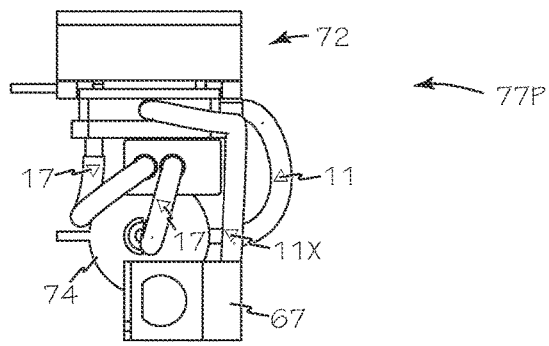
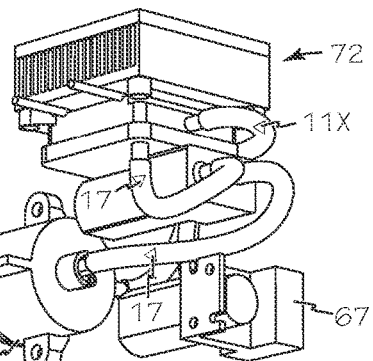
Fig. 10
Fig. 11
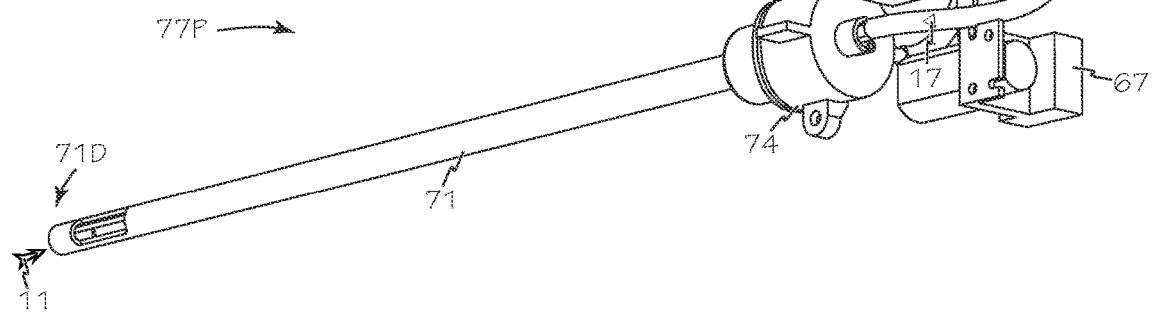
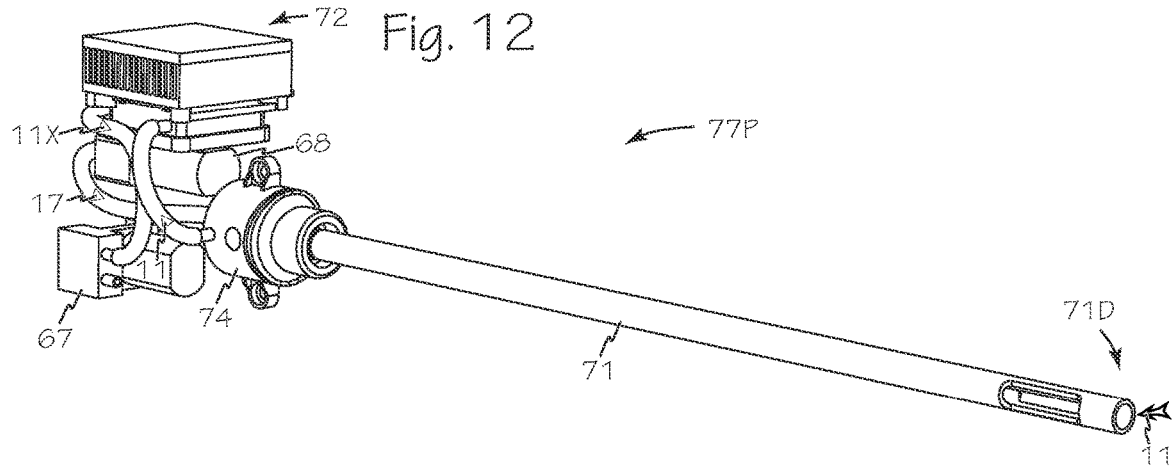
Fig. 12

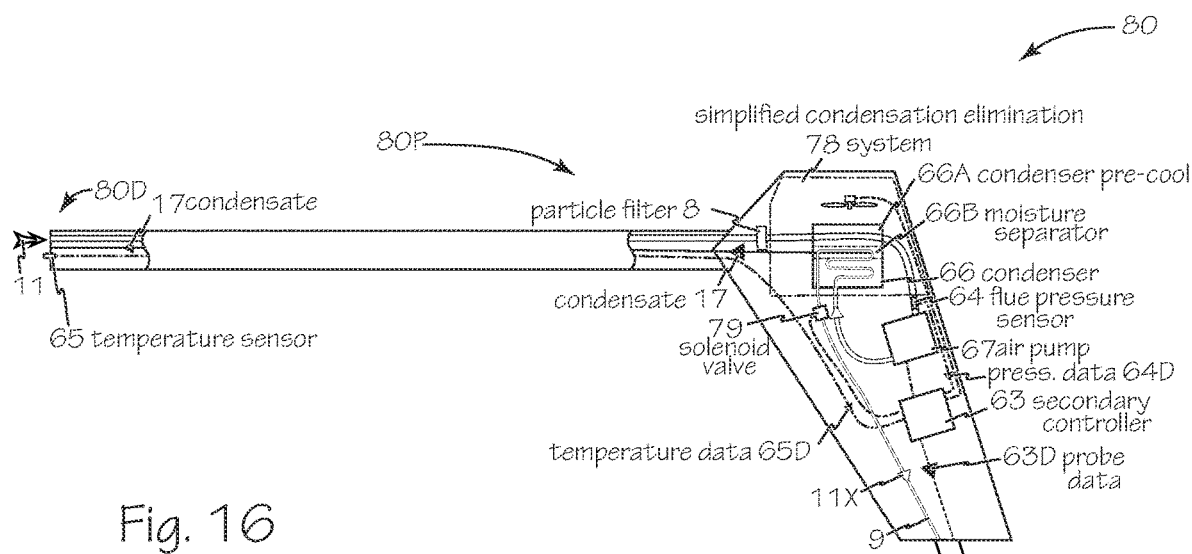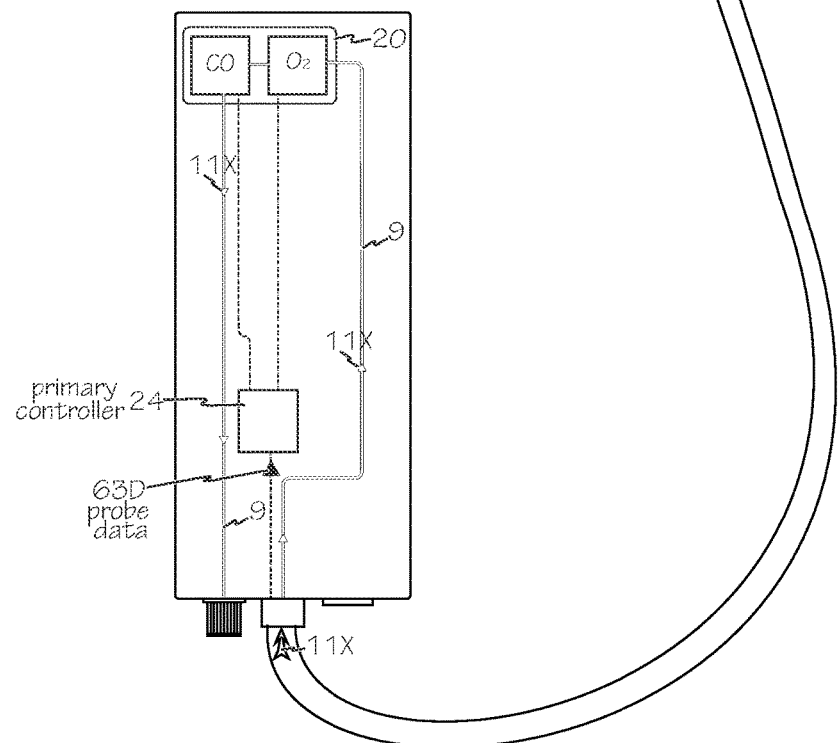
Fig. 16

COMBUSTION ANALYZER

This application is a continuation application of U.S. Utility application Ser. No. 17/166,888 filed Feb. 3, 2021 which is now U.S. Pat. No. 11,788,986, which is a continuation-in-part of now allowed, co-pending U.S. Utility Application Ser. No. 16/407,807 filed May 9, 2019 which claims priority to U.S. Provisional Application 62/676,804, filed May 25, 2018.

FIELD OF THE INVENTIONS

The inventions described below relate to the field of combustion analyzers.

BACKGROUND OF THE INVENTIONS

Conventional combustion analyzers include a water trap to collect condensed liquid from the stream of combustion by-products. The condensed liquid also contains many combustion by-products creating a toxic soup that must be disposed in a specific manner when the trap reaches capacity. In addition, the water traps are susceptible to freeze induced breakage if left full in low temperatures.

Many of the electrochemical sensor elements in conventional combustion analyzers contain liquid electrolyte and other elements that are highly reactive with oxygen. The flue gasses that the sensor elements are exposed to have a low percentage of free oxygen. However, when the combustion analyzer is not in use, the electrochemical sensors are exposed to air with about 21% oxygen. Consequently, the reactive elements of the electrochemical sensors are rapidly consumed and the electrolyte either dries out in low humidity or is diluted by attracting water in high humidity environments.

SUMMARY

The devices and methods described below provide for a combustion analyzer system that avoids the problems of collecting and disposing of hazardous condensate and preserves the reactive elements in the sensors when the system is not in use. The combustion analyzer system has an analyzer unit, a primary analysis probe and optional remote probes. The analyzer unit includes a condensation elimination unit and one or more electrochemical sensors to detect, for example, oxygen and carbon monoxide. The condensation elimination unit is operable to separate condensable vapors in the flue gas, or moisture in the flue gas, or both. Dry flue gas is directed to the sensor(s), and the condensed vapors or separated moisture is directed to a mister for dispersal or directed back into the flue for dispersal in the flue.

In an alternate configuration a primary analysis probe includes a secondary controller, a condenser/moisture separator and fan to cool and separate the combustion gas from the condensable liquid to return the liquid from the gas stream to the probe tip as liquid for injection into the flue. The primary analysis probe also includes temperature and pressure sensors in the probe tip. The analyzer unit includes two or more electrochemical sensors to detect at least oxygen and carbon monoxide and the primary controller. The analyzer unit also includes a means for sealing or isolating the electrochemical sensor inputs to prevent oxidation of the reactive elements and preserve the electrolyte when the unit is not in use.

BRIEF DESCRIPTION OF THE DRAWINGS

FIG. 7 is an illustration of an alternate combustion analyzer with the moisture separator and secondary controller in the probe and the primary controller in the analyzer unit.

FIG. 8 is a side view of the primary probe components for an alternate combustion analyzer with the condensation return system in the primary probe.

FIG. 9 is an exploded side view of the combustion analyzer system of FIG. 8.

FIG. 10 is a rear plan view of the combustion analyzer system of FIG. 8.

FIG. 11 is a bottom, right, rear perspective view of the combustion analyzer system of FIG. 8.

FIG. 12 is a top, left, front perspective view of the combustion analyzer system of FIG. 8.

FIG. 16 is an illustration of the alternate combustion analyzer of FIG. 7 with a simplified condensation system.

DETAILED DESCRIPTION OF THE INVENTIONS

Figure 1:
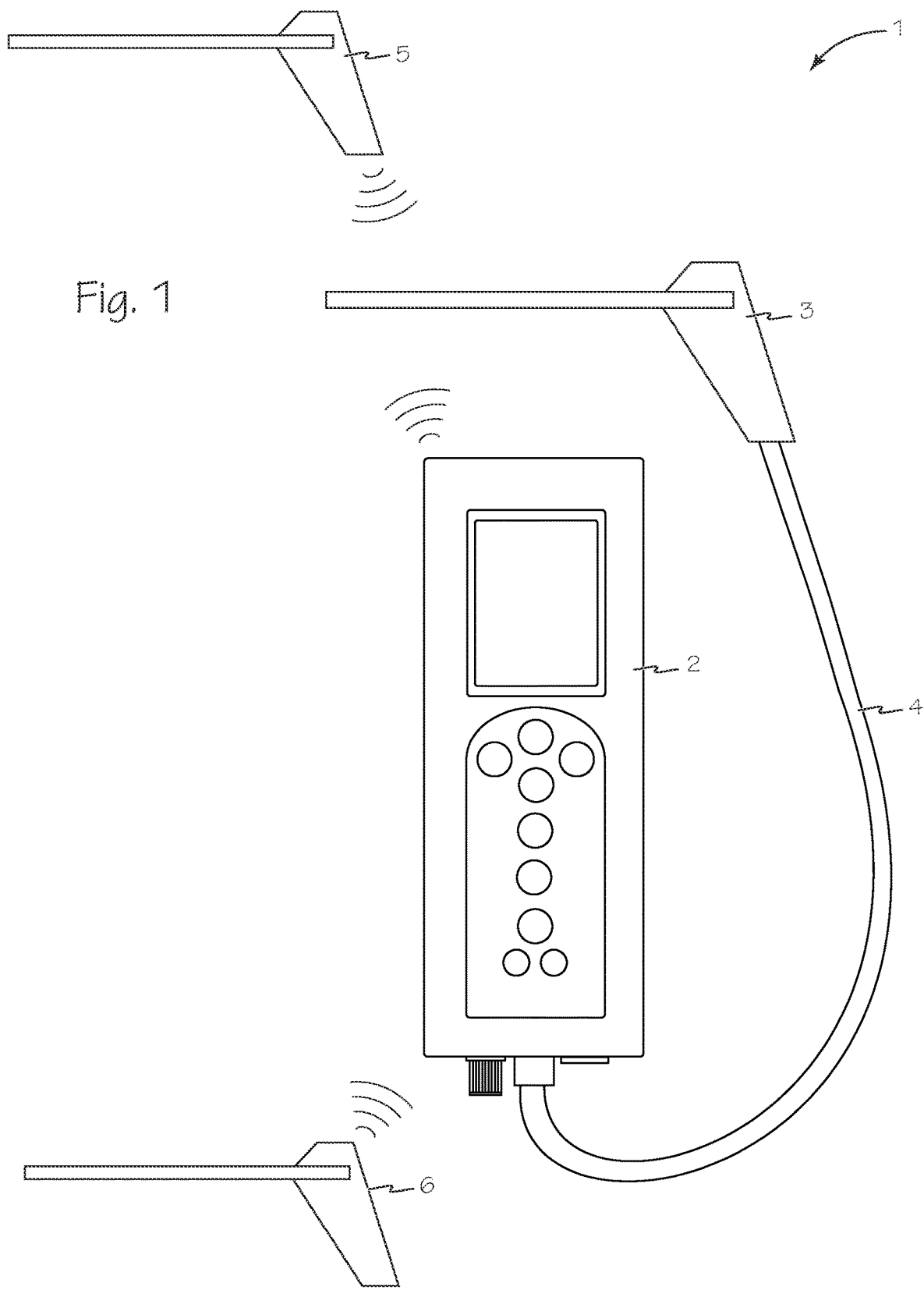
FIG. 1 is an illustration of a combustion analyzer system.

FIG. 1 is an illustration of combustion analyzer system 1. The combustion analyzer system 1 includes an analyzer unit 2 which is operatively connected to primary probe 3 via cable 4. One or more optional remote probes, such as probes 5 and 6, may communicate with analyzer unit 2 using any suitable technique.

Figure 2:
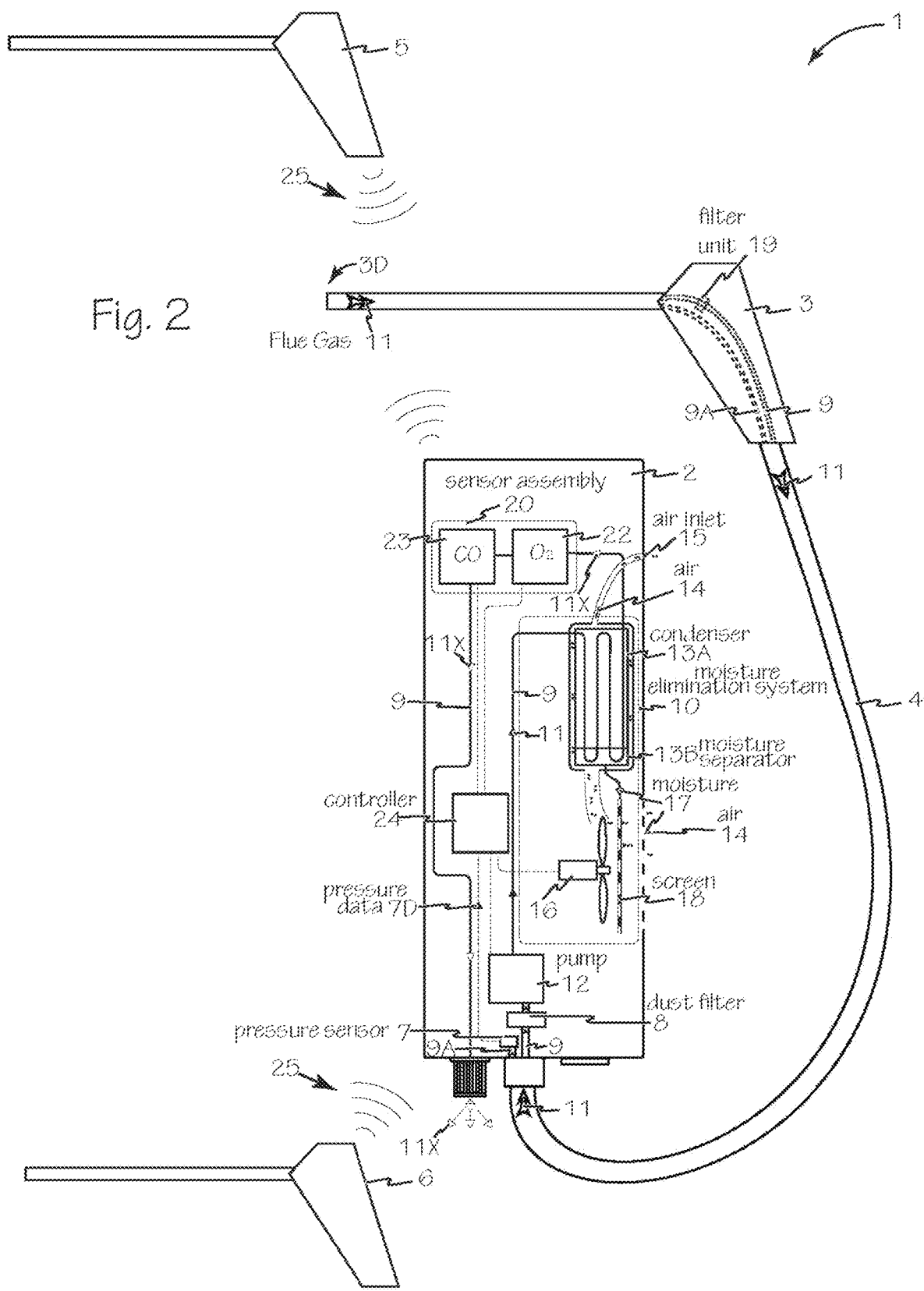
FIG. 2 is an illustration of some of the internal components of the combustion analyzer of FIG. 1.

The combustion analyzer unit 2 illustrated in FIG. 1 is shown in FIG. 2 with some of the internal components illustrated. The combustion analyzer unit 2 includes a condensation elimination system 10 that does not require emptying a liquid trap. Flue gas 11 is drawn into the analyzer unit 2 via an optional secondary filter, such as dust filter 8 by a pump 12. The flue gas is pumped into condenser 13A where the condensable gasses in the flue gas are condensed to liquid and separated from the flue gas by the relatively cool ambient air 14 being drawn from air inlet 15 and circulated around and through the condenser 13A by fan 16. The condensation elimination system 10 may also comprise a moisture separator 13B, either in lieu of or in addition to the condenser 13A, which operates to separate moisture from the flue gas. The condensed liquid, condensate 17, or moisture from the moisture separator 13B, is separated from the flue gas 11 and the condensate/moisture from the separator is conducted to any suitable atomizer, such as screen or net 18 where it is exhausted from the analyzer unit 2 with the ambient air 14. The screen serves to atomize or aerosolize the condensate or moisture 17 from the separator 13B. Any other suitable technique for aerosolizing the condensate/ moisture from the separator may also be used, such as a mist generator or misting nozzle. The acid content of the separated moisture may be minimized by the use of filter unit 19 (a ceramic catalyst filter for example) in primary probe 3 to filter the NOx and the SOx out of flue gas 11. Dust filter 8 and the filter unit 19 may be located together or separately in the primary probe or the analyzer unit.

The filtered, dry flue gas 11X is moved from the condenser/moisture separator 13B into a sensor assembly 20 by pump 12. In sensor assembly 20, one or more electrochemical sensors, such as oxygen sensor 22 and CO sensor 23, are exposed to flue gas 11X and each sensor produces an electrical signal corresponding to the level of their respective compound that is present in the dry, filtered flue gas 11X. The electrochemical sensors in sensor assembly 20 are operatively connected to controller 24 which analyzes the electrical signals from the electrochemical sensors and produces an output signal corresponding to the measured characteristics of dry, filtered flue gas 11X. The controller 24 includes one or more microprocessors and is operatively connected to the fan 16, the pump 14, the primary probe 3, the sensors 22, 23 and other components capturing data or providing feedback to a user. The controller 24 is operable to turn the fan 16 on when liquid is present in the moisture separator 13B.

Flue gas conduit 9 conducts the flue gas 11 to the condensation elimination system 10 and to the sensor assembly 20. Gas pressure sensor 7 is located in the analyzer unit 2 and is operably connected to the distal end 3D of the primary probe 3 via flue gas pressure conduit 9A, which enable the pressure sensor 7 to detect the draft pressure of the flue. A stable pressure sensor, such as pressure sensor 7, maintains accuracy specifications for about 30 minutes and this enables the analyzer unit to monitor the draft pressure and provide the pressure data 7D to the controller 24 for display to a user.

Optional remote probes 5 and 6 measure chemical, thermal and other characteristics of a combustion system, such as flue pressure, and these characteristics are transmitted as signals 25 to controller 24 and may be displayed on the analyzer unit 2 and/or any suitable mobile device.

Figure 3:
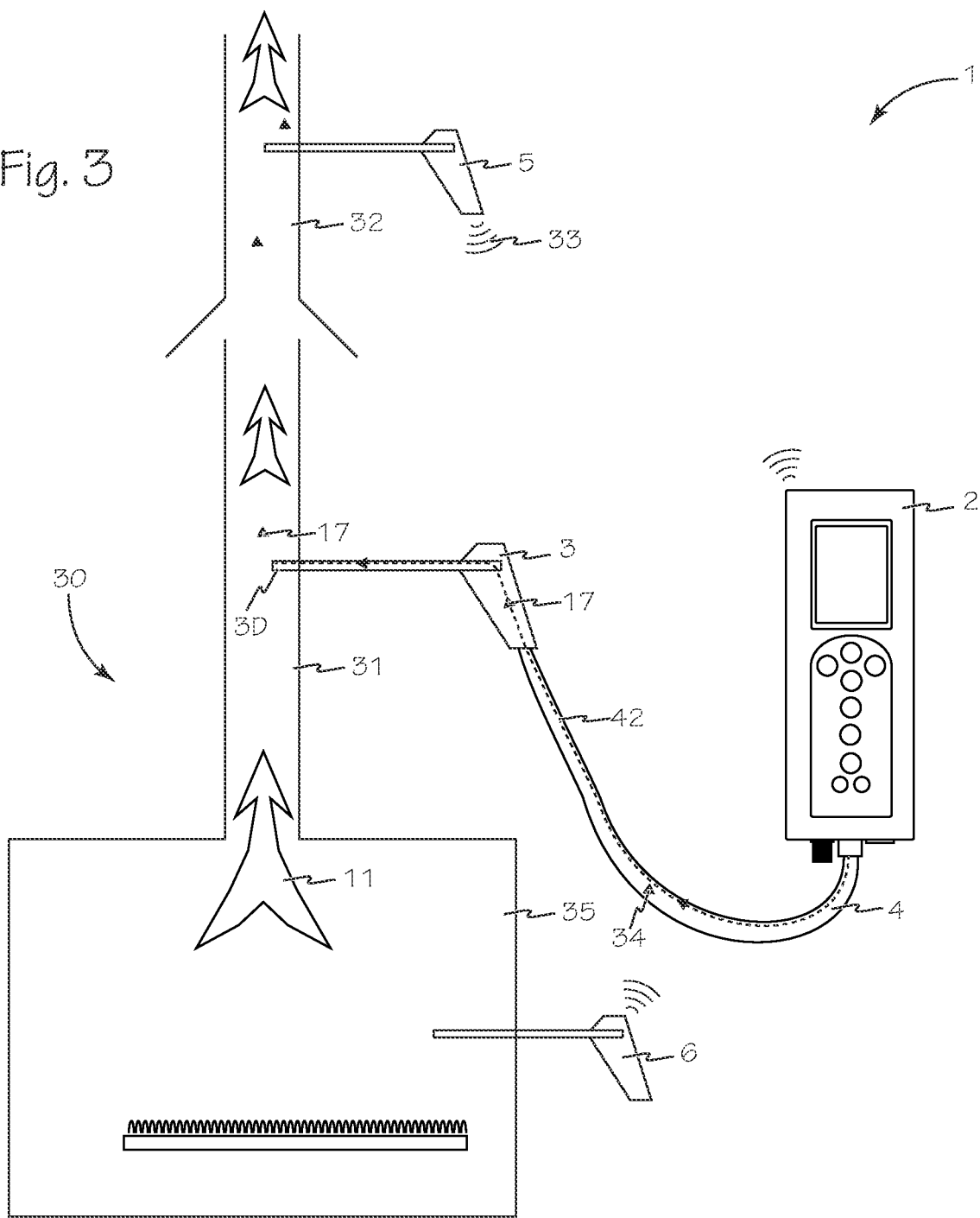
FIG. 3 illustrates the use of the combustion analyzer of FIG. 1 in an installed heating system.

FIG. 3 illustrates the use of the combustion analyzer of FIG. 1 in combustion system 30. In use, analyzer unit 2 is connected to primary probe 3 and distal end 3D is inserted into the primary system flue 31. Remote probe 5 is inserted into secondary system flue 32 to provide reference data 33 to compare to primary data 34 from the primary probe 3. Reference data 33 may include flue pressure, temperature, humidity/relative humidity and air flow rate. Firebox measurements may be accomplished by using a remote probe, such as probes 5 or 6, inserted into firebox 35.

Figure 4:
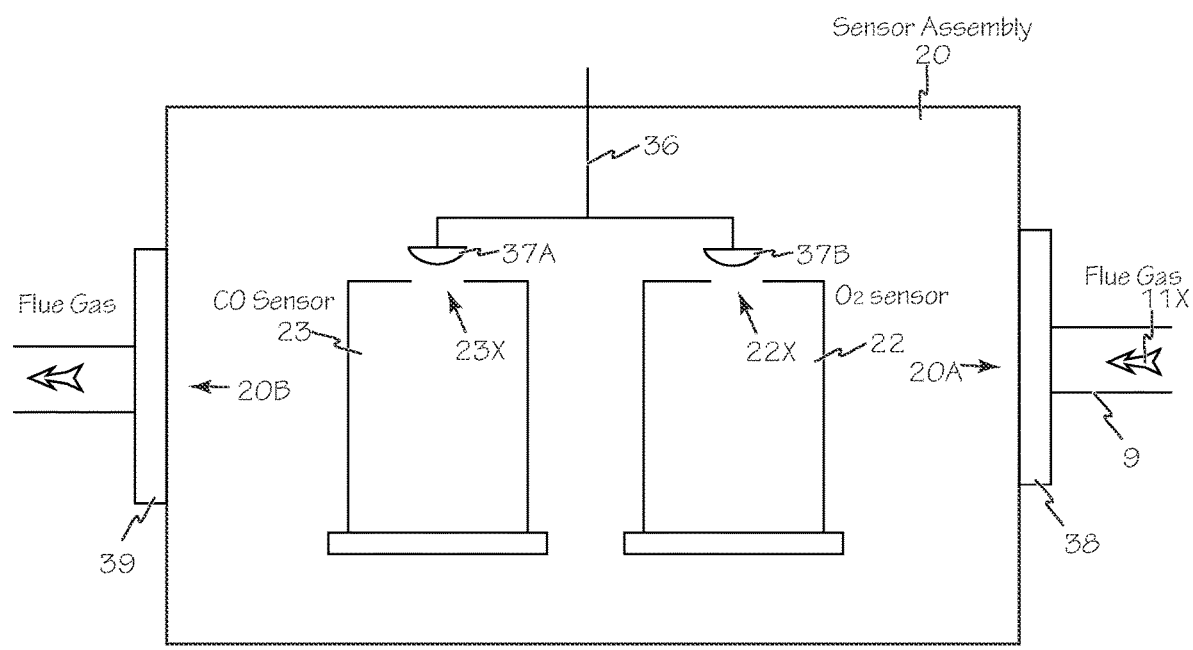
FIG. 4 is a close up illustration of the sensor assembly of the combustion analyzer of FIG. 1.

FIG. 4 is a close up illustration of sensor assembly 20. Sensor sealer 36 is a plunger that applies any suitable sealing element to each sensor orifice. Sealing element 37A seals electrochemical sensor orifice 23X and sealing element 37B seals electrochemical sensor orifice 22X. One or more optional moisture filters, such as moisture filters 38 and 39, may be provided at gas input 20A and gas output 20B respectively.

Figure 5:
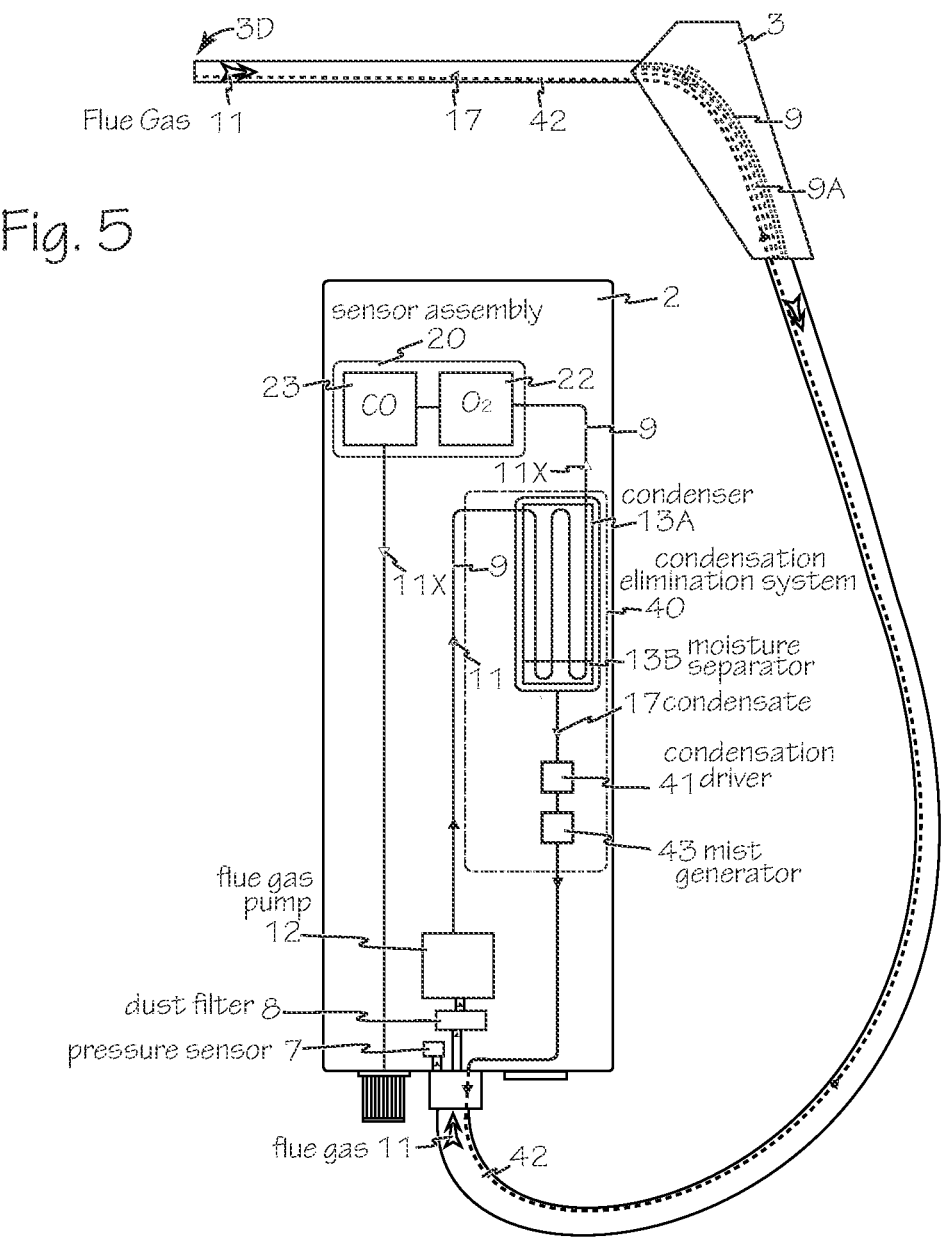
FIG. 5 is an illustration of the combustion analyzer system of FIG. 1 with an alternate condensation system.

The condensation elimination system 40 of FIG. 5 removes moisture from the flue gas 11 to be tested and returns the moisture to the primary system flue 31 as condensate 17 using the leakage pressure of flue gas pump 12 through the condenser 13A. The collected condensation may optionally be driven to the distal end 3D of the probe with condensate pump or driver 41 and condensate return line 42, which conducts the condensate 17 from the condensation elimination system 40 to the distal end 3D of the primary probe 3 and back into the primary flue 31, as illustrated in FIG. 3. Condensate driver 41 may be located in any suitable location in the condensation elimination system 40. The condensation driver 41 may be any suitable fan or pump. An optional mist generator 43 may use any suitable technology, such as a piezo inducer, to reduce condensate to a mist for conduction and reintroduction into the primary flue. The optional mist generator 43 may also be used in place of the metal screen or net 18.

Figure 6:
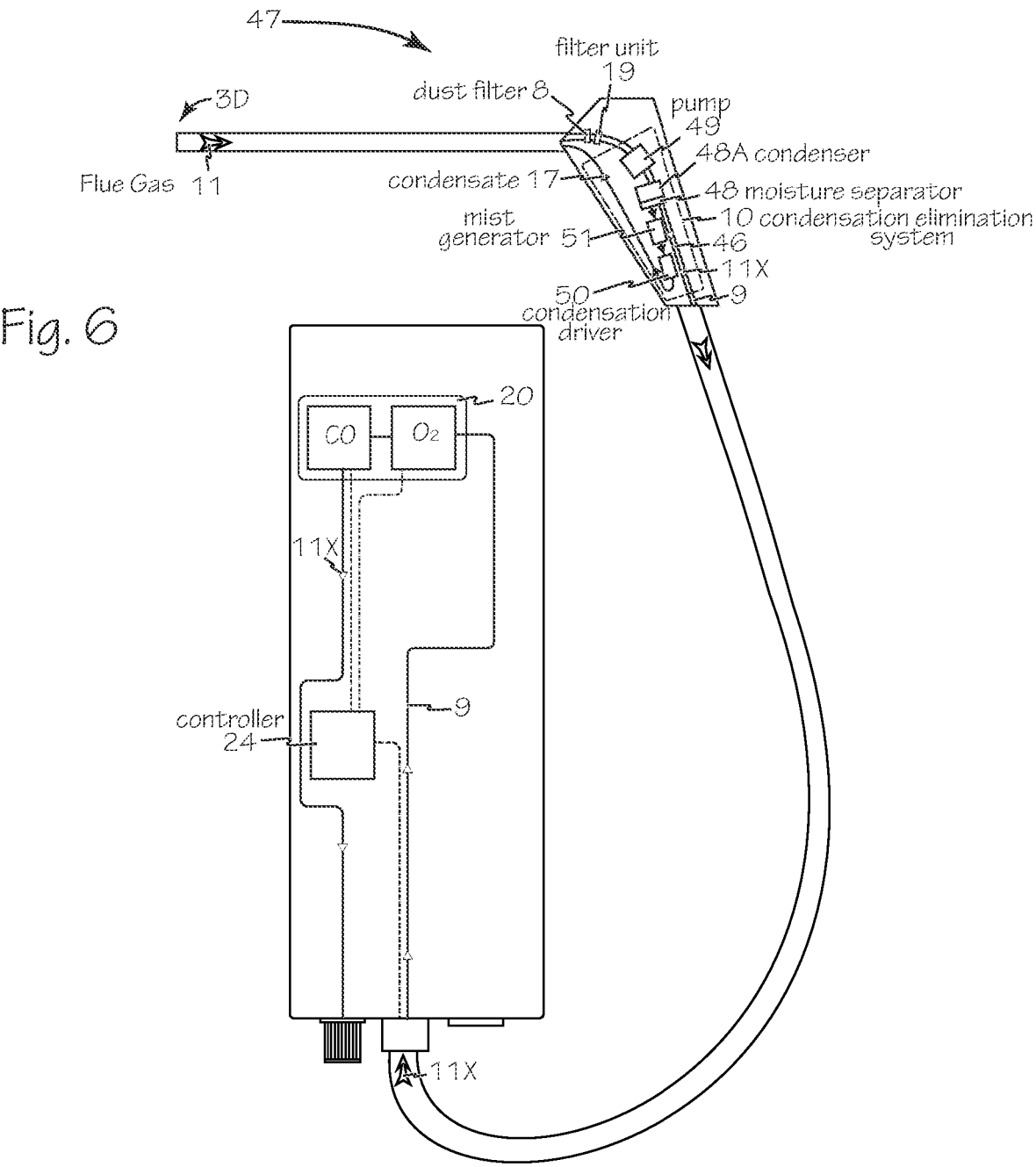
FIG. 6 is an illustration of the combustion analyzer system of FIG. 1 with the condensation system in the primary probe.
Figure 13:
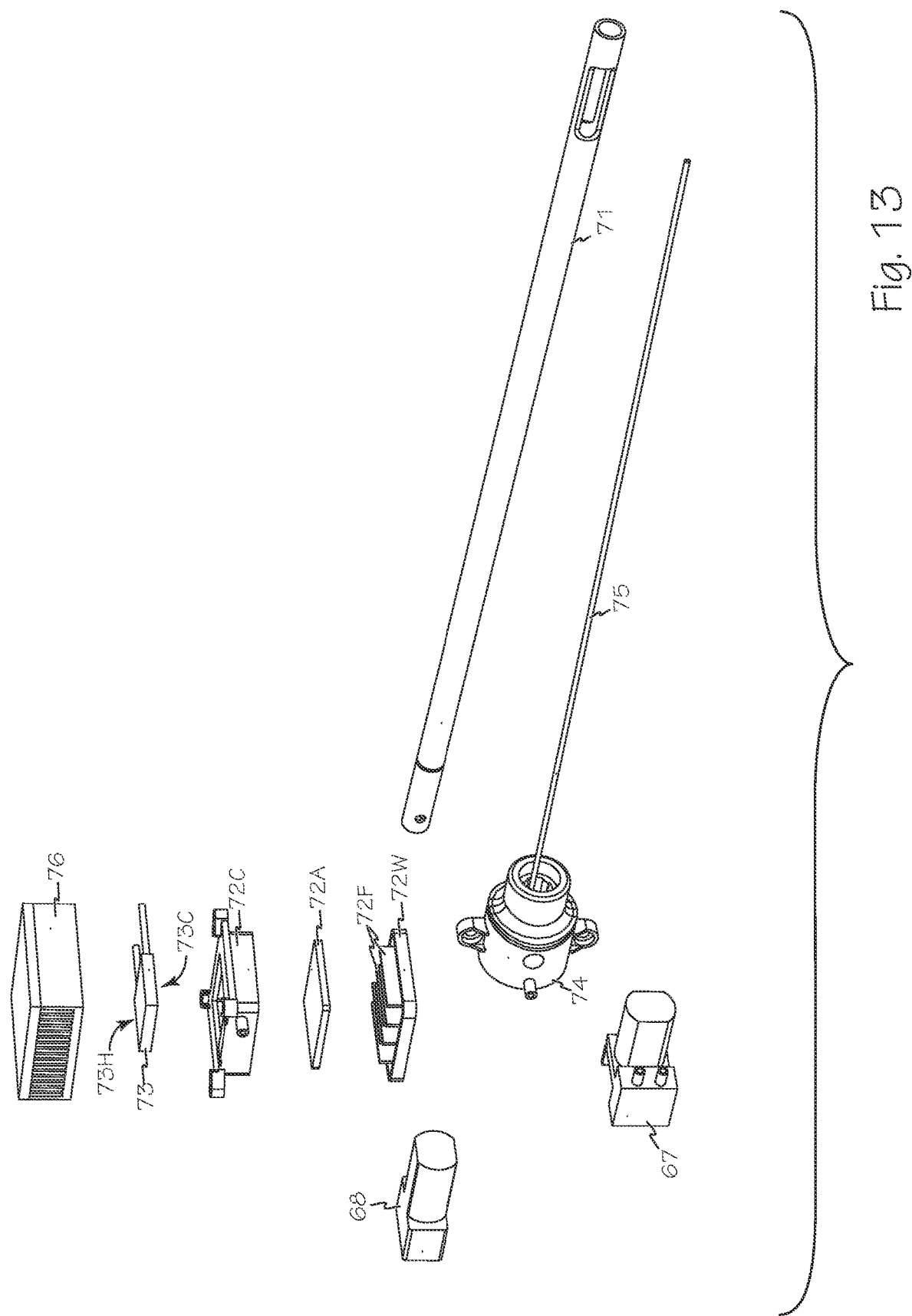
FIG. 13 is a front exploded perspective view of the combustion analyzer system of FIG. 8.
Figure 14:
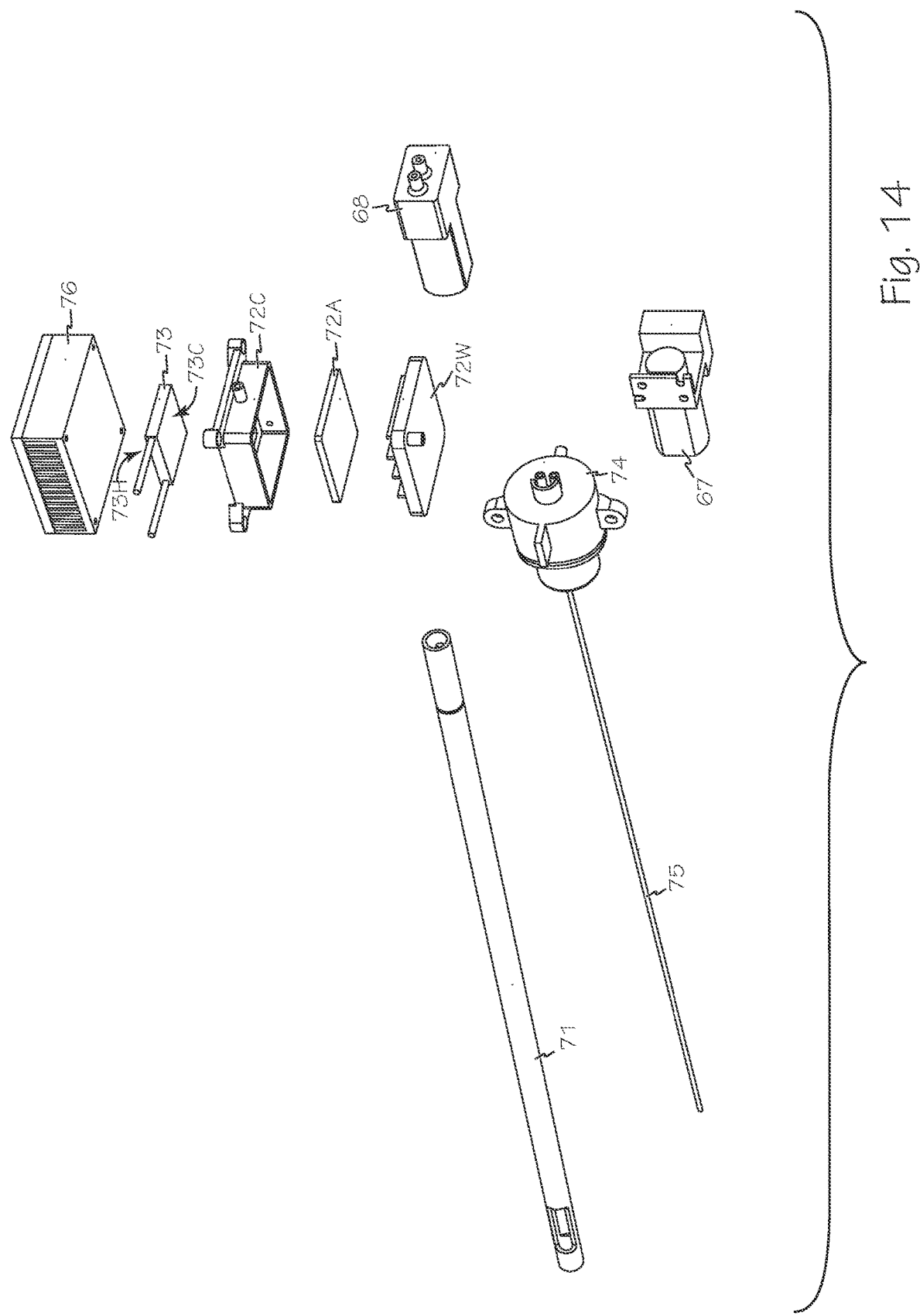
FIG. 14 is a rear exploded perspective view of the combustion analyzer system of FIG. 8.

FIG. 6 is an illustration of the combustion analyzer system of FIG. 1 with the condensation system 10 in the primary probe 47. Flue gas 11 is drawn into the primary probe where it is filtered as discussed above and is then pumped into moisture separator 48 by any suitable pump, such as pump 49. Pump 49 may be located, as shown between the probe distal end 3D and the condenser 48A, or in any other suitable location, such as between the condenser 48A and the sensor assembly 20, such as for example, location 46. The dry, filtered flue gas 11X is then conducted to the sensor assembly 20 for testing as discussed above. Condensate 17 is pumped from the moisture separator 48 using any suitable condensation driver, such as pump 50. Optional mist generator 51 may also be used to reduce the condensate to a mist for conduction and reintroduction into the primary flue.

Alternate combustion analyzer system 60 is illustrated in FIG. 7. System 60 includes primary probe 61 which houses the condensation system 62, a secondary controller 63, as well as the optional pressure sensor 64, the optional temperature sensor 65 and the condenser 66. Pressure data 64D and temperature data 65D may be collected by the secondary controller 63 and combined with other probe data and are forwarded to the primary controller 24 as probe data 63D for display to the user and transmission to other devices. Flue gas 11 is drawn into the primary probe where it is filtered as discussed above and is then drawn through the condenser pre-cool chamber 66A by any suitable pump such as air pump 67 and then through the moisture separator 66B. The dry, filtered flue gas 11X is then conducted to the sensor assembly 20 for testing as discussed above. Condensate 17 is pumped from the condenser 66 out through the distal end 61D of the primary probe using any suitable condensation driver such as pump 68.

An alternate condensation elimination system 7270 is illustrated in FIGS. 8 through 14. Condensation elimination system 72 may be part of any suitable primary probe, such as probes 3, 61, 77P or 80P. Flue gas 11 is drawn in through the gas sample tube 71 and through probe inlet adapter 74 by any suitable gas pump, such as gas pump 67. Flue gas 11 is drawn into condensation elimination system 72 and specifically through condenser cap 72C. Within the condenser cap 72C, the flue gas 11 is then drawn across the condenser fins 72F. The condenser fins 72F are cooled by direct contact between the cool side 73C of Peltier cell 73 and the heat transfer plate 72A which is in contact with condenser fins 72F. Heat transfer plate 72A is operatively connected to the cool side 73C of Peltier cell 73 through condenser cap 72C, as illustrated in FIG. 9. Any moisture that condenses in condensation system 72, such as condensate 17, is contained within condenser well 72W. Condensate 17 is pumped from the condensation system 72 through the probe inlet adapter 74 out through condensate return tube 75 to the distal end 71D of the gas sample tube using any suitable condensation driver such as pump 68. The dry, filtered flue gas 11X is then conducted to the sensor assembly 20 via gas tube 9 for testing as discussed above. The hot side, side 73H of Peltier cell 73 is cooled by fan 76 operably connected to hot side 73H.

Alternatively, the flue gas sample 11 may enter the probe through the gas sample tube 71 and it is collected in probe inlet adapter 74, gas pump 67 draws the gas sample 11 in and propels it to condenser cap 72C and then to the sensor assembly 20. With this configuration there is no need for a condensation driver, such as pump 68, the pressure applied by the gas pump 67 to the gas sample 11 in the condenser cap 72C will pressurize the condenser cap 72C and force condensate 17 through the condenser well 72W and out through condensate return tube 75 back into the flue.

Figure 15:
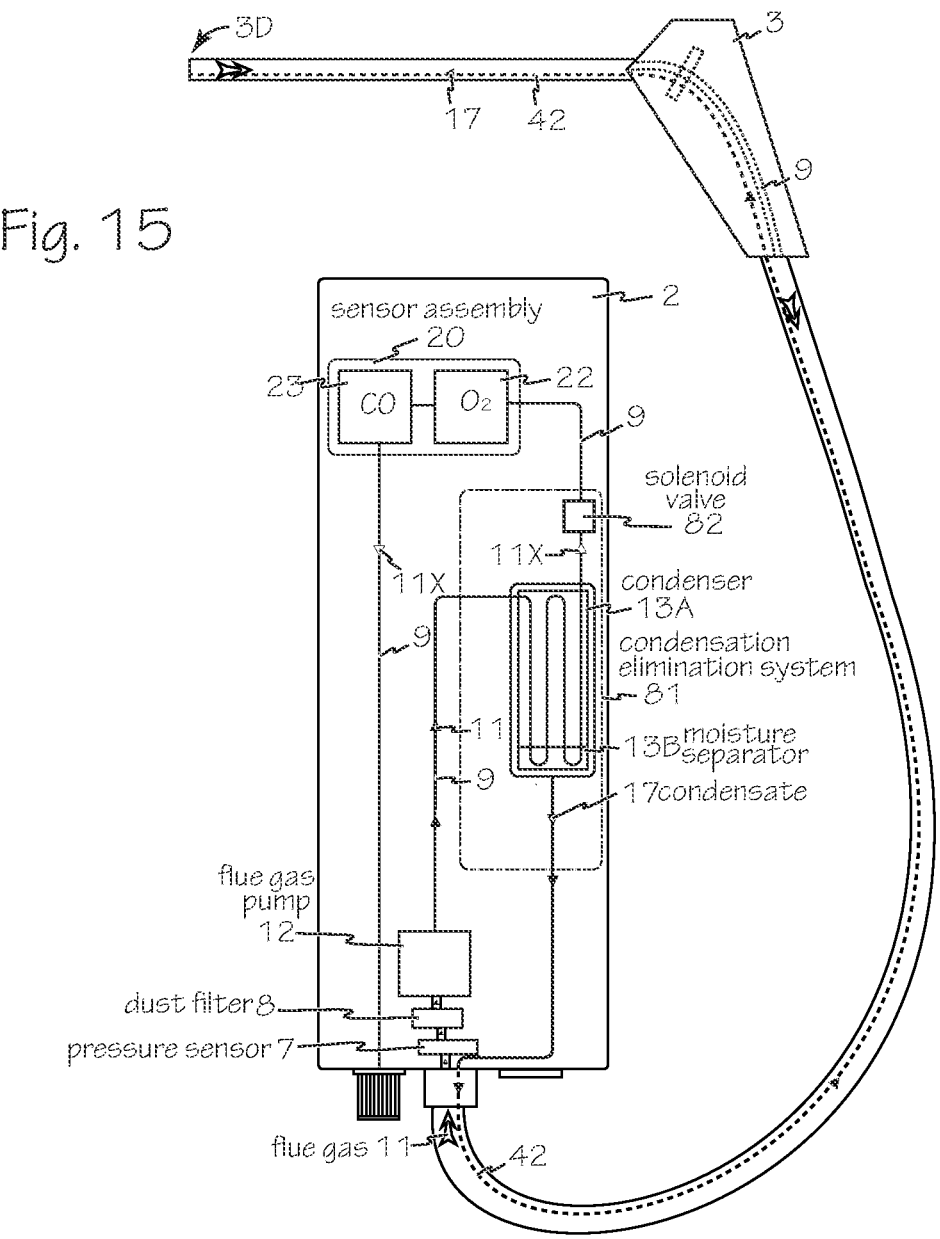
FIG. 15 is an illustration of the combustion analyzer system of FIG. 5 with a simplified condensation system.

The condensation elimination system 81 of FIG. 15 removes moisture from the flue gas to be tested and returns the moisture as condensate 17 back through the primary probe 3 to the primary system flue much like the system 40 of FIG. 5. The simplified condensation elimination system 81 eliminates a condensation pump and uses solenoid valve 82 to periodically pressurize the condenser 13A and moisture separator 13B to force the condensate 17 into condensate return line 42 and to pressurize the condensate return line 42. The solenoid valve 82 may remain open most of the time and the pressure from the flue gas pump 12 will push the flue gas 11 through the sensors 22 and 23 as required and some small amount of the pressure will pressurize the condenser 13A and moisture separator 13B to slowly move the condensate 17 out to the distal end 3D of probe 3. When the solenoid valve 82 is closed periodically the full pressure of the flue gas pump 12 will push the condensate 17 through the condensation elimination system 81 and back to the probe and into the flue being analyzed. Solenoid valve 82 may be located in any suitable location in the combustion analyzer system.

Alternate combustion analyzer system 80 is illustrated in FIG. 16. System 80 has a simplified condensation elimination system 78 that differs from combustion analyzer system 60. Flue gas 11 is drawn into the primary probe 80P where it is filtered as discussed above and is then pushed through the moisture separator pre-cool chamber 66A by any suitable pump, such as air pump 67, and then through the moisture separator 66B. The dry, filtered flue gas 11X is then conducted to the sensor assembly 20 for testing as discussed above. In the simplified condensation elimination system 78, the water pump of system 60 is replaced with solenoid valve 79. Condensate 17 is forced from the moisture separator 66B out through the distal end 80D of the primary probe 80P using the pressure of the flue gas pump 67. When the solenoid valve 79 is closed periodically, the full pressure of the flue gas pump 67 will push the condensate 17 through the condensation elimination system 78 and back into the flue being analyzed. Solenoid valve 79 and flue gas pump 67 may be located in any suitable location in the combustion analyzer system 80.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. A combustion analyzer system comprising:
   a combustion analyzer unit having one or more electrochemical sensors and a primary controller;
   a primary probe having a distal end and a condensation elimination system operably connected to the combustion analyzer unit, the condensation elimination system comprising:
   a condenser having a moisture separator, the condenser operably connected to receive combustion gas within the primary probe and condense and separate any liquid from the combustion gas into condensate and to conduct the combustion gas to the electrochemical sensors via a flue gas conduit;
   a return line operatively connected between the condenser and the distal end of the primary probe;
   an air pump operably connected to the flue gas conduit to pressurize the condenser, the moisture separator and the flue gas conduit; and
   a water pump operably connected between the condenser and the distal end of the primary probe operable to pump liquid to the distal end of the primary probe; and
   one or more secondary probes operable to communicate with the combustion analyzer unit.

2. The combustion analyzer system of claim 1 wherein the primary probe further comprises a secondary controller operatively connected to the primary controller, the air pump and the water pump.

3. The combustion analyzer system of claim 1 wherein the condenser further comprises a pre-cooler.

4. The combustion analyzer system of claim 1 wherein the primary probe further comprises:
   a chemical filter unit.

5. The combustion analyzer system of claim 4 wherein the primary probe further comprises:
   a dust filter.

6. The combustion analyzer system of claim 1 wherein the primary probe further comprises:
   a dust filter.

7. The combustion analyzer system of claim 1 wherein the primary probe further comprises:
   a pressure sensor operably connected to a secondary controller.

8. The combustion analyzer system of claim 1 wherein the primary probe further comprises:
   a temperature sensor operably connected to a secondary controller.

9. The combustion analyzer system of claim 1 wherein the primary probe further comprises:
   a pressure sensor and a temperature sensor wherein the sensors are operably connected to a secondary controller.

10. The combustion analyzer system of claim 1 further comprising:
    one or more secondary probes operable to communicate with the combustion analyzer unit.

11. A method of collecting flue gas for analysis and disposing of condensate from the flue gas comprising the steps:
    opening a sensor sealer operably connected to an analyzer unit comprising sensors operable to detect one or more constituents of the flue gas;
    collecting flue gas from an active flue;
    cooling the flue gas and separating liquid condensates to create a stream of dry flue gas for analysis and a stream of condensate;
    disposing of the condensate stream; and
    conducting the dry flue gas to the analyzer unit.

12. The method of claim 11 wherein the step of disposing of the condensate stream comprises:
   returning the condensate to the active flue for disposal.

13. A combustion analyzer system comprising:
   a combustion analyzer unit having a condensation elimination system and one or more electrochemical sensors;
   a primary probe operably connected to the combustion analyzer unit, the primary probe operable to conduct dry flue gas to the one or more electrochemical sensors; and
   a sensor sealer in the combustion analyzer unit operatively connected to the one or more electrochemical sensors to seal the one or more electrochemical sensors when not in use.

14. The combustion analyzer system of claim 13 further comprising:
   one or more secondary probes operable to communicate with the combustion analyzer unit.

15. The combustion analyzer system of claim 14 wherein the condensation elimination system comprises:
   a condenser operably connected to receive combustion gas from the primary probe and condense condensable vapors and separate any liquid from the combustion gas as condensate;
   an atomizer operably connected to the condenser to conduct the condensate from the condenser; and
   a fan oriented to force air through a screen and blow air and condensate out of the combustion analyzer unit.

16. The combustion analyzer system of claim 15 wherein the condensation elimination system further comprises:
   a controller operably connected to the fan to turn the fan on when liquid is present in the condenser.

17. The combustion analyzer system of claim 14 wherein the condensation elimination system comprises:
   a moisture separator operably connected to receive combustion gas from the primary probe and separate moisture from the combustion gas as condensate;
   an atomizer operably connected to a condenser to conduct the condensate from the moisture separator; and
   a fan oriented to force air through a screen and blow air and condensate out of the combustion analyzer unit.

18. The combustion analyzer system of claim 17 wherein the condensation elimination system further comprises:
   a controller operably connected to the fan to turn the fan on when liquid is present in the moisture separator.

\* \* \* \* \*